United States Patent
Mathaes et al.

(10) Patent No.: US 10,801,913 B2
(45) Date of Patent: Oct. 13, 2020

(54) DEVICE AND METHOD FOR IMPROVED CLOSURE INTEGRITY TESTING

(71) Applicant: Lonza Ltd, Visp (CH)

(72) Inventors: Roman Mathaes, Basel (CH); Anja Matter, Sissach (CH); Sarah Pelaez, Basel (CH); Hanns-Christian Mahler, Loerrach (DE); Atanas Koulov, Basel (CH)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 16/646,691

(22) PCT Filed: Sep. 13, 2018

(86) PCT No.: PCT/EP2018/074719
§ 371 (c)(1),
(2) Date: Mar. 12, 2020

(87) PCT Pub. No.: WO2019/053113
PCT Pub. Date: Mar. 21, 2019

(65) Prior Publication Data
US 2020/0276394 A1   Sep. 3, 2020

Related U.S. Application Data

(60) Provisional application No. 62/558,513, filed on Sep. 14, 2017.

(30) Foreign Application Priority Data

Sep. 14, 2017 (EP) .................... 17190996
Apr. 27, 2018 (EP) .................... 18169894

(51) Int. Cl.
G01M 3/22 (2006.01)
G01M 3/20 (2006.01)
A61M 5/32 (2006.01)

(52) U.S. Cl.
CPC ............ G01M 3/229 (2013.01); G01M 3/202 (2013.01); A61M 5/3202 (2013.01)

(58) Field of Classification Search
CPC ........ G01M 3/20; G01M 3/202; G01M 3/226; G01M 3/229
(Continued)

(56) References Cited

U.S. PATENT DOCUMENTS 4,813,268 A * 3/1989 Helvey ................. G01M 3/205
73/40.7
6,398,771 B1 6/2002 Gustafsson et al.
(Continued)

FOREIGN PATENT DOCUMENTS

DE 102006017958 10/2007
WO WO9737628 10/1997
WO WO9946572 9/1999

OTHER PUBLICATIONS

International Preliminary Report for PCT/EP2018/074719 dated Feb. 1, 2019, 6 pages.
(Continued)

*Primary Examiner* — Nathaniel J Kolb
(74) *Attorney, Agent, or Firm* — Dority & Manning, P.A.

(57) ABSTRACT

The present invention relates to a method and a device for determining the robustness and tolerance of pre-filled containers, in particular pre-filled syringes (PFS) against accidental movement of flexible parts, specifically tip cap and/or plunger movement due to external influences by measuring the leakage rate of a test medium in correlation to a movement of a flexible parts.

21 Claims, 7 Drawing Sheets

(58) Field of Classification Search
USPC .............................. 73/40, 46, 40.7, 49.2, 49.8
See application file for complete search history.

(56) References Cited

U.S. PATENT DOCUMENTS

| | | | |
|---|---|---|---|
| 9,903,782 B2 * | 2/2018 | Fisk ...................... | G01M 3/205 |
| 2009/0277249 A1 | 11/2009 | Polster et al. | |
| 2011/0080183 A1 * | 4/2011 | Hala ...................... | F04B 51/00 |
| | | | 324/700 |
| 2015/0316440 A1 * | 11/2015 | Fisk ...................... | G01M 3/202 |
| | | | 73/40.7 |
| 2018/0045653 A1 * | 2/2018 | Angermund ....... | G01N 21/9054 |

OTHER PUBLICATIONS

International Search Report for PCT/EP2018/074719 dated Nov. 27, 2018, 3 pages.

* cited by examiner

US 10,801,913 B2

DEVICE AND METHOD FOR IMPROVED CLOSURE INTEGRITY TESTING

CROSS REFERENCE TO RELATED APPLICATIONS

This application is the U.S. National Stage entry of International Application Number PCT/EP2018/074719 filed under the Patent Cooperation Treaty having a filing date of Sep. 13, 2018, which claims priority to European Patent Application No. 17190996.3 having a filing date of Sep. 14, 2017, European Patent Application No. 18169894.5 having a filing date of Apr. 27, 2018, and U.S. Patent App. No. 62/558,513 having a filing date of Sep. 14, 2017, which are incorporated herein by reference.

BACKGROUND OF THE INVENTION

Pre-filled syringes (PFS) receive increasing attention as primary packaging and administration systems of choice for injectable drug products. This can be explained by several benefits PFS offer over the conventional glass vial, rubber stopper and crimp cap primary packaging combination. For example, PFS shift the point of care from hospital to convenient self-administration at the patient's home. In addition, the risk of contaminations and dosing errors is minimized.

Besides these benefits, pre-filled syringes are associated with complex, process-specific challenges and require adequate product development. A key factor in the development of PFS-based products for parenteral use is the analysis of container closure integrity (CCI) over its intended shelf-life. A breach of CCI is a significant concern for patient safety.

Pre-filled syringes can be provided in a broad variety of types, most of which have in common that they comprise a body or barrel (1), a plunger (2), a needle cannula (3), and a tip cap (4), commonly comprising a closed end portion (6), preferably made from rubber or silicone. The tip cap (4) can additionally comprise a rigid needle shield (RNS) (7), as schematically illustrated in FIG. 1.

PFS require complex components and manufacturing processes. Compared to a rubber stopper of a conventional vial, small dimensional variabilities of the rigid needle shield (RNS) as well as moulding defects may compromise the CCI. PFS featuring a removable needle shield and a movable plunger are susceptible to external stress factors with a potential impact on CCI. For example, pressure differences during air shipment can impact the tip cap position and thus CCI.

A few methods are available for container closure integrity tests (CCIT) of PFS and other containers, e.g. the microbial container closure integrity test (mCCIT), or physical container closure integrity tests (pCCIT) such as mass spectrometry-based helium leak testing (B. D. Morrical at al, PDA Journal of Pharmaceutical Science and Technology 2007, 61 (4), 226-236). Although there is no clear practical guidance or preference by regulatory authorities for a specific CCIT, the helium leak method is currently the most sensitive CCIT and can be considered as the gold standard for container closure system (CCS) qualification.

A possible reason for a pre-filled and capped syringe, which may generically also be called a container with a flexible part, which would be the cap of the syringe, to start leaking, may be an external influence, which may exert its effect for example during packaging or transport, and by which the flexible part is moved over such a distance that the container starts leaking. Therefore it was desirable to have an indication of the tolerance of the flexible part against movement until a leak occurs.

The object of this invention is to provide a means for testing and ensuring the quality of combination product containing a PFS or other container, in particular the quality, robustness, integrity and/or sensitivity of the CCS of pre-filled or pre-fillable syringes.

SUMMARY OF THE INVENTION

The inventors were able to develop a new method to analyse the robustness of a seal of a flexible part, which is sealing a container, preferably a cartridge, a vial or a pre-filled syringe. The invention further relates to a device allowing to carry out the new method and to the use of said in device in the developed method.

BRIEF DESCRIPTION OF THE FIGURES

The figures are included for illustrative purposes only and are not intended to be limiting the invention.

DETAILED DESCRIPTION OF THE INVENTION

The present invention relates to a method and a device for determining the robustness and tolerance of pre-filled containers, in particular pre-filled syringes (PFS) against accidental movement of flexible parts, specifically tip cap and/or plunger movement due to external influences by measuring the leakage rate of a test medium in correlation to a movement of a flexible parts. The method is suitable for any type of pre-filled container, and particularly suitable for pre-filled syringes comprising removable closure means.

Figure 1:
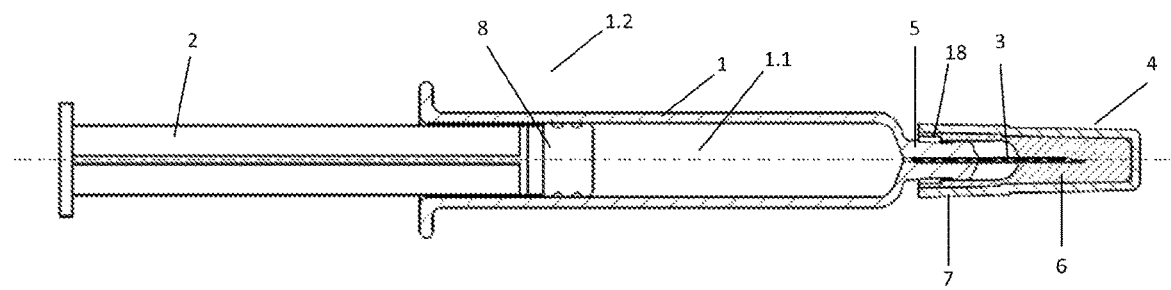
FIG. 1: Illustration of a pre-filled syringe.

A typical PFS (see FIG. 1) comprises a barrel (1), separating a syringe interior (1.1) and a syringe exterior (1.2), a plunger (2), a needle cannula (3), a tip cap (4). The needle cannula (3) is fixed in and passes through a cone shaped tip (5) of the barrel (1). Some syringes may comprise a stopper (8) attached to the plunger. In some embodiments of the invention, the plunger and—if present—the stopper of the syringe are removed before carrying out the method steps described below.

Accordingly, a typical pre-filled syringe comprises two flexible parts that can affect container closure integrity, namely the tip cap and the plunger.

The tip cap (4) preferably comprises a closed end portion (6). The closed end portion preferably comprises a flexible material, for example rubber or silicone, and acts as a seal in addition to providing protection for and from the needle cannula. The cap can additionally comprise a rigid needle shield. The rigid needle shield provides further support and protection and is preferably made from a rigid polymeric material.

Some syringes additionally comprise a circumferential rib or ring at the syringe tip (18), which is preferably made of the same material as the syringe barrel. Said ring or rib, may provide additional protection stability for the tip cap.

The barrel (1) and the plunger (2) may be made of any suitable material. Preferred materials include glass and/or polymeric material. In some embodiments, the barrel comprises a mixture of polymers.

The method is preferably used on syringes intended to be used as pre-filled syringes. As such the method allows for the selection, qualification or quality control of specific syringe-tip cap combinations.

In a first aspect, the invention relates to a method for determining the robustness of a seal of a flexible part of a container comprising the steps of:

a) providing a container comprising at least one flexible part, wherein said at least one flexible part comprises a sealing means;

b) said sealing means is sealing the interior (1.1) of the container from the exterior of the container (1.2);

c) providing a fluid connection (9) between the interior of the container with a detection device for a test medium (10);

d) exposing the exterior of the container to an atmosphere comprising said test medium (10);

e) moving the flexible part of the container in a direction away from the container until the detection device detects the test medium above a predefined threshold value;

f) determining the distance by which the flexible part was moved in step e).

Said container might be any container comprising a flexible part. The flexible part might be a cap, a stopper or a plunger. The container can be any container suitable for applications as pre-filled container, preferably suitable for pharmaceutical applications, preferably a container for containing pharmaceuticals, preferably for containing pharmaceuticals under sterile conditions, such as containers which are used for providing formulated drugs, which are ready for medical application on a patient, and in an amount necessary for said medical application. The volume of such containers is usually 100 mL or less, preferably 50 mL or less, more preferably 25 mL or less, even more preferably 10 mL or less, especially 5 mL or less. Such a container is e.g. a syringe or a cartridge or a vial.

The exterior of the container (1.2) is also called the exterior atmosphere (1.2).

In a specific aspect, the invention relates to a method for determining the robustness of a seal of a flexible part of a syringe comprising the steps of:

a) providing a syringe comprising a barrel (1) and at least one flexible part, wherein said at least one flexible part comprises a sealing means;

b) said sealing means is sealing the interior (1.1) of the syringe from the exterior of the syringe (1.2);

c) providing a fluid connection (9) between the interior of the syringe with a detection device for a test medium (10);

d) exposing the exterior of the syringe to an atmosphere comprising said test medium (10); e) moving the flexible part of the syringe in a direction away from the syringe until the detection device detects the test medium above a predefined threshold value;

f) determining the distance by which the flexible part was moved in step e).

In a preferred embodiment of the invention, the flexible part is a tip cap and/or a plunger. In a specific embodiment, the flexible part is a plunger. In a further specific embodiment, the flexible part is a tip cap.

The invention will be described with reference to a syringe comprising a tip cap and/or plunger. However, it is clear to the skilled person that the description and specific embodiments can be readily generalized to any container comprising a flexible part with sealing means.

In a specific aspect of the invention, the invention relates to a method for determining the robustness of the sealing of a syringe by a tip cap against accidental movement. In other words, the invention relates to a method for determining how much accidental movement on a tip cap residing on the tip or on an inlet of a syringe can occur without causing the seal formed between the syringe and the tip cap to lose its integrity.

In a specific embodiment, invention relates to a method for determining the robustness of a tip cap seal of a syringe comprising the steps of:

a) providing a syringe comprising a barrel (1) and a tip (5), wherein the tip (5) is covered with the tip cap (4) such as to form a seal between the tip (5) and the tip cap (4); b) said seal is sealing the interior (1.1) of the syringe against the exterior of the syringe (1.2);

c) providing a fluid connection (9) between the interior of the syringe with a detection device for a test medium (10);

d) exposing the exterior of the syringe to an atmosphere comprising said test medium (10);

e) moving the tip cap of the syringe in a direction away from the syringe until the detection device detects the test medium above a predefined threshold value;

f) determining the distance by which the tip cap was moved in step e).

In an alternative specific embodiment, the invention relates to a method for determining the robustness of a plunger seal of a syringe comprising the steps of:

a) providing a syringe comprising a barrel (1) and a plunger (5), wherein the plunger comprises a sealing means;

b) said sealing means is sealing the interior (1.1) of the syringe against the exterior atmosphere (1.2);

c) providing a fluid connection (9) between the interior of the syringe with a detection device for a test medium (10);

d) exposing the exterior of the syringe to an atmosphere comprising said test medium (10);

e) moving the plunger of the syringe in a direction away from the syringe until the detection device detects the test medium above a predefined threshold value;

f) determining the distance by which the plunger was moved in step e). In a preferred specific embodiment, the plunger comprises a rubber stopper.

Preferably, the detection of the test medium by the detection device is done in form of a concentration, of a flow rate or of an amount, more preferably in form of a flow rate, of the test medium.

Figure 2A:
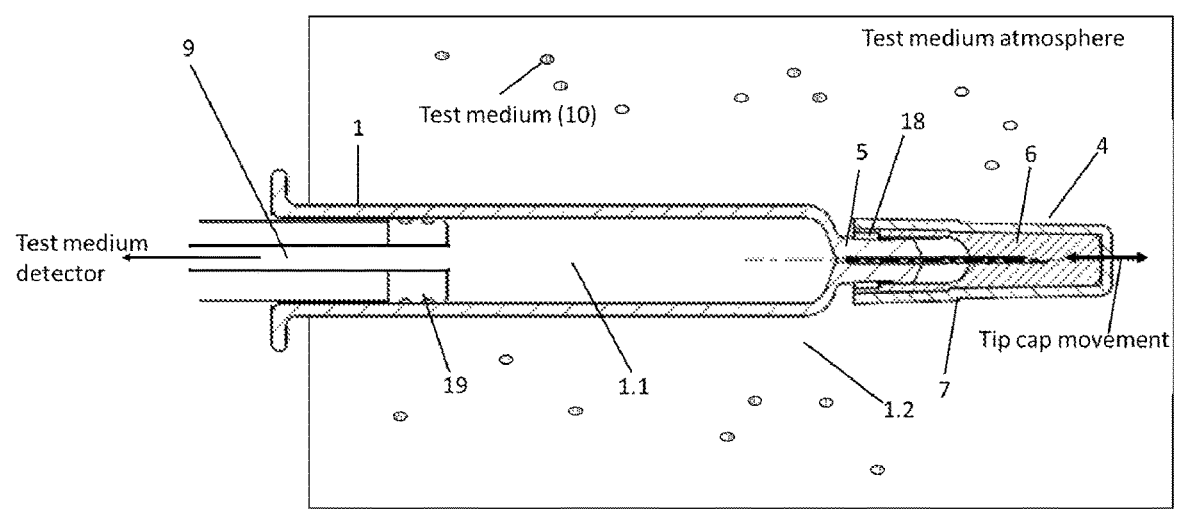
FIG. 2: Schematic illustration of the method. 2A: Closed syringe in an atmosphere of a test medium, sealed and closed by the tip cap. 2B: Movement of the tip cap within acceptable range does not comprise the sealing ability of the tip cap. 2C: Compromised sealing of the tip cap after tip cap movement.
Figure 2B:
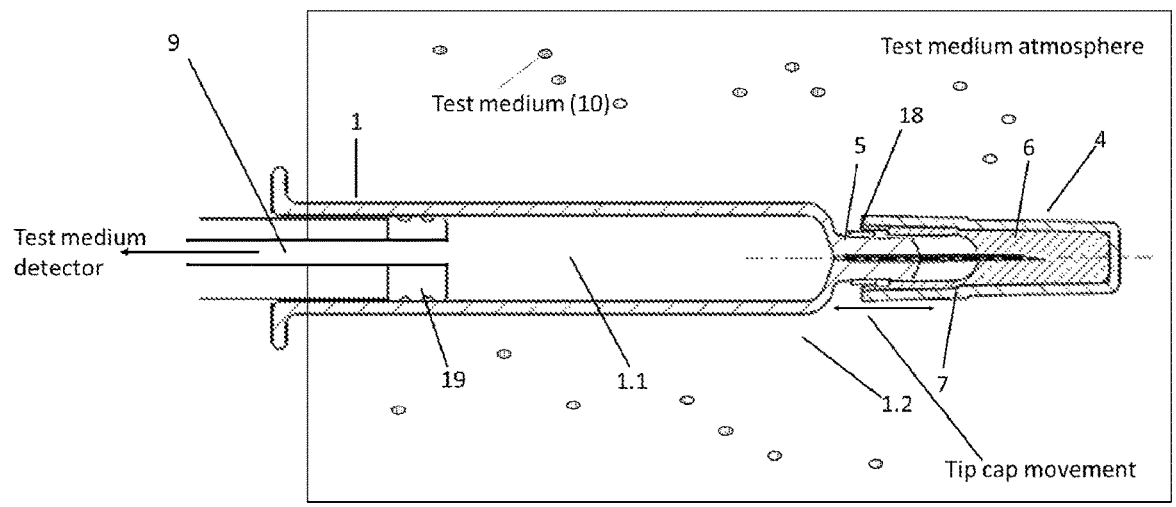
Figure 2C:
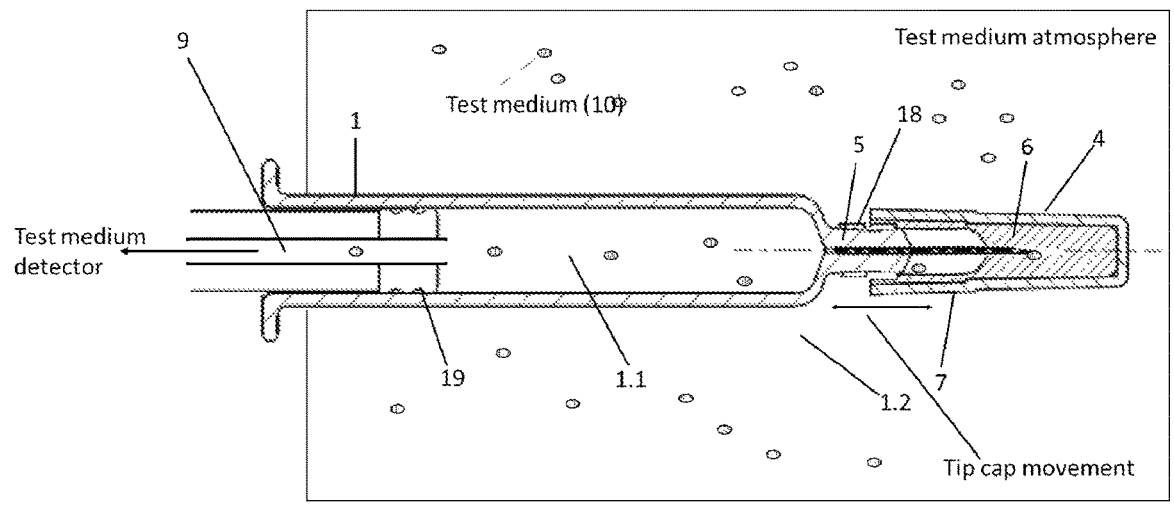

Initially, the detection device which is in fluid connection (9) with the interior space of the syringe will normally detect no (or only traces of) test medium as the interior of the syringe is kept separate from exterior atmosphere due to the seal formed between the tip cap (4) and the tip (5) of the syringe or between the plunger (2) and the barrel (1) of the syringe (FIG. 2A). Typically, minute movements of the tip cap and/or the plunger would not destroy the integrity of the seal either (FIG. 2B). However, when the tip cap (4) and/or plunger (2) is moved over an increasing distance, there typically comes a distance when the seal between the tip cap (4) and/or plunger (2) and the tip or the barrel loses its integrity, a leak between the tip cap and the syringe and/or a leak between the plunger and the barrel appears, with the consequence that test medium from the syringe exterior begins to flow into the syringe through said leak, and the detection device begins to detect the test medium (FIG. 2C) in a concentration, flow rate or an amount above a predefined threshold value.

The distance determined in step f) at which the seal loses its integrity corresponds to an indicator of robustness of the flexible part seal against accidental movement. A higher distance indicates a higher tolerance against accidental movement and, thus, a higher robustness.

The method is a relative method. The distance of movement is determined based on the position of the plunger (2) and/or tip cap (4) at the start of the method. Preferably, the tip cap and/or plunger has not been moved prior to the method of the invention.

The method is suitable for any type of syringe. Preferably, the syringe is a glass or polymer syringe. In one embodiment, the syringe is a polymer syringe. In a further embodiment, the syringe is a glass syringe. In a specific embodiment, the syringe is a polymer syringe and the polymer is selected from polyethylene, polypropylene, cyclic olefin polymer, cyclic olefin copolymer and mixtures thereof. In a particular embodiment of the invention, the syringe is a polymer syringe made from cyclic olefin polymer or cyclic olefin copolymer.

The threshold value can for example be a concentration, or an amount or a flow rate of the test medium and which is used for differentiating between a seal that is still intact and a seal that has lost its integrity. in one embodiment, the threshold value is a flow rate.

Some polymer syringes show some degree of permeability for certain test mediums, in particular gases, which should be taken into account when selecting the threshold value. For example, the measurement of a polymer syringe, which may be permeable to the test medium might be performed at specific points of time or after specific intervals of time after exposure of the syringe exterior to the test medium.

In some embodiments, the syringe preferably comprises a needle cannula (3), which is protected by the tip cap (4). The tip cap preferably comprises a closed end portion (6), preferably of rubber or silicone, which acts as sealing means for the needle cannula (3) and the syringe tip (5), and a rigid needle shield (7), preferably made from polymeric materials. The plunger (2) and any rubber stopper (8) of the syringe are preferably removed or manipulated to allow a fluid connection to the detector.

In different embodiments of the invention, the syringe preferably comprises a plunger (2) with a rubber stopper (8) and in specific embodiments the tip (5), needle cannula (3) and tip cap (4) have been removed or manipulated to allow a fluid connection to the detector.

An advantage of the method is that it is compatible with several known and available leak detection methods and devices, which can be used after respective modifications of said devices in order to practice it.

The test medium may be any suitable fluid or gas which can be readily detected by an appropriate detector that allows specific and sensitive detection of said test medium. In some preferred embodiments of the invention, the detection is performed using mass spectrometry.

In a particular embodiment, the detection device is a mass spectrometer.

Preferably, the test medium is a gas. In a specific embodiment, the test medium is a gas selected from the group consisting of Hydrogen, Argon and Helium. In a particular embodiment of the invention, the test medium is Helium.

The method can be performed with atmospheric pressure or with a pressure above atmospheric pressure at the exterior of the syringe. In general, the pressure at the syringe exterior may be above atmospheric pressure, however, the pressure should be compatible with the syringe. Preferably, the pressure at the syringe exterior is at about atmospheric pressure.

It is preferred that the interior of the syringe is evacuated. The evacuation may be performed by the detection device, or by a further device, such as a conventional vacuum pump. Preferably, the pressure inside the syringe is less than 100 mbar, more preferably less than 50 mbar, even more preferably less than 25 mbar, especially less than 20 mbar, more especially less than 10 mbar, even more especially less than 5 mbar, in particular less than 1 mbar.

The exterior of the syringe is exposed to the test medium. It is preferred that the exterior is exposed to an atmosphere comprising the test medium. More preferably, the exterior is exposed to an atmosphere comprising at least 50%, even more preferably, at least 75%, especially at least 80%, more especially at least 85%, even more especially at least 90%, in particular at least 95%, of test medium, the % being % by volume based on the total volume of the atmosphere to which the exterior of the syringe is exposed to.

The exposure of the exterior of the syringe to an atmosphere of test medium can be realized by exposing the exterior of the syringe to a constant flow of the test medium. Preferably, the exposure is performed in a chamber which is flooded by a constant flow of the test medium at or above atmospheric pressure.

Figure 3:
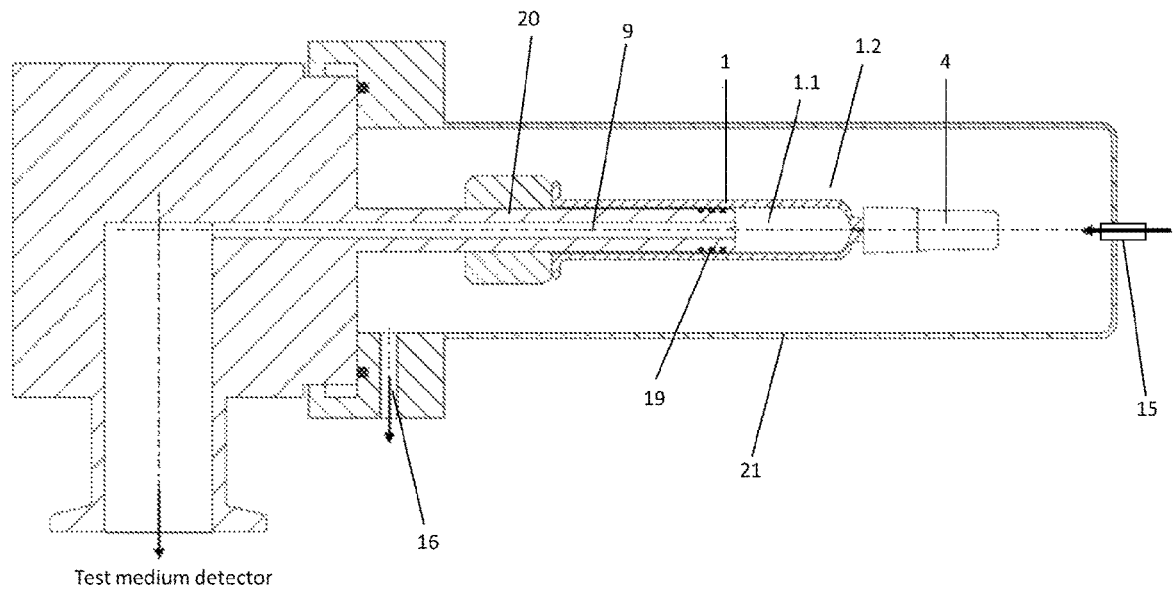
FIG. 3: Schematic illustration of a specific setup for the analysis of tip cap movement.
Figure 4:
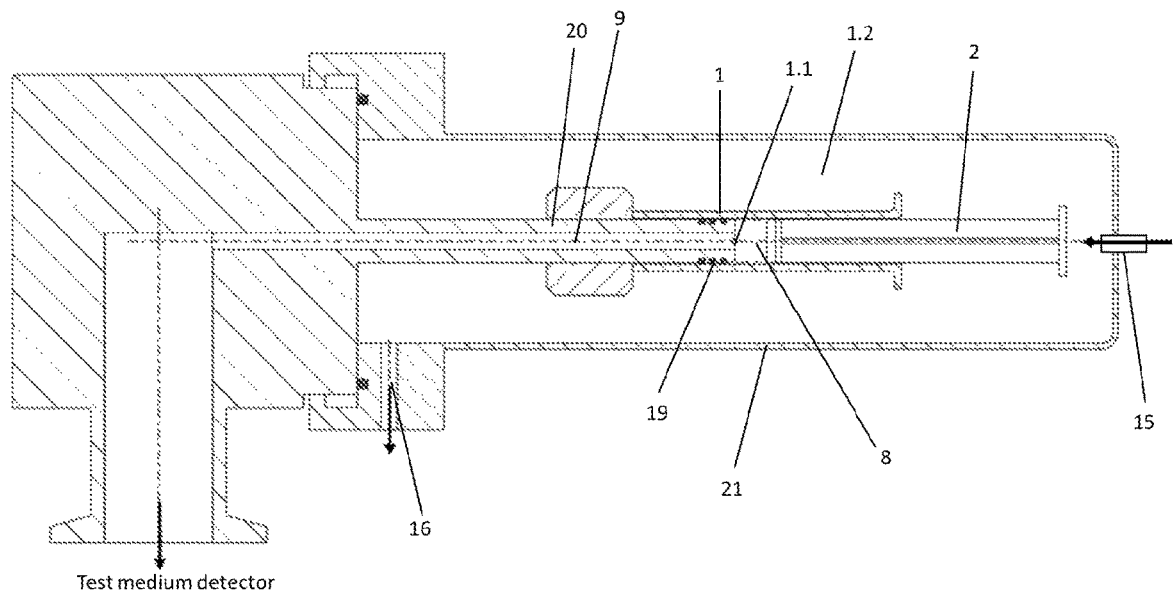
FIG. 4: Schematic illustration of a specific setup for the analysis of plunger movement.

Preferred non-limiting embodiments are shown in FIG. 3 or 4. The syringe (1) with a tip cap (4) (FIG. 3A) or a plunger (2) optionally with a rubber stopper (8) (FIG. 4A), sealing the syringe interior (1.1) and the syringe exterior (1.2), is attached to a holder (20), which comprises a sealing means (19) completely sealing the syringe interior (1.1) from the exterior (1.2). The holder (20) with the syringe is placed in a chamber (21) comprising an inlet for a test medium (15) and an outlet (16), which allows controlling the pressure of said test medium. The syringe interior (1.1) is in fluid connection (9) with a test medium detector.

In a particular preferred embodiment, the method is based on He-leak detection, wherein the test medium is He and the detector is a He detector, more preferably a mass spectrometric He-detector.

Accordingly, in a preferred embodiment, the exterior is exposed to an atmosphere comprising Helium, also with all the possible embodiments of the amounts of He as the test medium as described herein.

The atmosphere comprising the test medium may be generated by exposing the syringe to a constant flow of the test medium, preferably to a constant flow of He. In some embodiments, the exposure is performed in a chamber, which is constantly flooded by the test medium, more preferably flooded by Helium under atmospheric pressure, see also FIGS. 3A and 4A. In different embodiments, the syringe is exposed to a constant stream of test medium.

The method is suitable for the identification of the acceptable movement of the tip cap and/or plunger, for example utilized for a particular batch of syringes.

It is preferred that in step e) the tip cap and/or plunger is moved in a straight line, preferably along the axis defined by the syringe barrel, alternatively defined by the direction in which the needle cannula extends.

The tip cap and/or plunger might be moved continuously or sequentially. If the tip cap and/or plunger is moved continuously, it is preferred that the tip cap and/or plunger is moved with a constant movement rate. Said constant movement rate should be sufficiently slow to allow for simultaneous detection of the test medium.

The stop point of movement is dependent on the test medium and on the detection method.

Preferably, the movement is stopped at the point where the detection of the test medium exceeds a predefined threshold value. This detection of the test medium above a predefined value indicates a respective flow of the test medium from the exterior of the syringe into the interior of the syringe. Said threshold value is for example dependent on the initial state or the initial localization of the tip cap on the syringe at the beginning of the test, on the application of the syringe and on the intended usage.

The tip cap and/or plunger can be moved manually or automatically. It is preferred, that the tip cap and/or plunger is moved in a controlled manner, allowing precise and defined movement.

The movement rate of the tip cap and/or plunger should be in correlation with latency of the detection of the test medium, in order to allow detection of the effective distance of movement at which the test medium is detected above the predefined threshold. If the movement rate is too fast with respect to the latency of the detection, obviously detection of the threshold value will happen later than a leak actually has occurred, so the measured distance will be too big. The latency of the detection depends on the various factors, such as the pressure of the test medium at the exterior of the syringe, the concentration of the test medium in the exterior atmosphere, the geometry of the detection device, the pressure at the interior of the syringe. Just as possible examples and in some embodiments of the inventions, the tip cap and/or plunger is moved with a movement rate of about 1 mm/min. in Some embodiments the movement rate is about 0.2 mm/10 s. In some embodiments, the movement rate is 0.1 mm/10 s.

In a specific embodiment of the invention, the method is used for quality control. In this particular method, the tip cap and/or plunger are moved a predefined distance and the amount of test medium is detected. The control is deemed passed if the device detects the test medium below a predefined threshold value after the the tip cap and/or plunger have moved said predefined distance.

In a preferred embodiment, the flexible part is moved with a moving apparatus. In a specific embodiment, the tip cap is moved with a tip cap moving apparatus. Said cap moving apparatus can allow automatic or manual or automatic and manual movement of the flexible part. In a particular embodiment, said cap moving apparatus can allow automatic or manual or automatic and manual movement of the tip cap.

An advantage of a tip cap moving apparatus is minimal disturbance of the tip cap, thus excluding other factors, such as external pressure fluctuations, which for example usually occur if the tip cap and/or plunger is moved manually, and which can influence the test results, for example by influencing the robustness of the sealing abilities of the tip cap.

If the method is based on the detection of helium as described above, it is preferred that the movement is stopped, once the detector detects a predefined He flow rate into the interior of the syringe. The threshold should be defined in accordance with the intended use. For example, the US pharmacopeia chapter <1207> suggests a threshold of a He-flow rate of $6\times10^{-6}$ (mbar*L)/s for He leak tests in closure integrity evaluation (USP<1207>, Package Integrity Evaluation-Sterile Products. pp 1700-1707).

It is preferred that the detection device has a sensor or other means of detection for the test medium, which are in fluid connection with the interior of the syringe, wherein the whole fluid connection between interior of the syringe and detection device is sealed from the exterior atmosphere.

It is preferred that the total internal volume of the test device is as small as possible, to allow the detection of small fluid streams with low flow rates, also to have a low latency of detection.

A further advantage of the method according of the invention, is the possibility to perform the method at different temperatures. As the PSF are stored and transported under different temperature conditions, the method allows to simulate such influences.

In a preferred embodiment, the method according to the invention is performed at room temperature. Preferably, the method is performed at a temperature between about 22 and 28° C., more preferably between about 24 and 16° C., most preferably at a temperature of about 25° C.

However, the method might be performed at higher or lower temperatures, in order to analyse the robustness of the syringe/tip cap combination at different conditions. In some embodiments, the method is performed at temperature of about or less than 20° C. In a further embodiment, the method is performed at a temperature of about or less than 15° C. In another embodiment, the method is performed at a temperature of about or less than 10° C. In yet another embodiment the method is performed at a temperature of about or less than 5° C.

The method might also be performed at higher temperatures. In some embodiments, the method is performed at a temperature of about 28° C. or above. In some embodiments, the method is performed at a temperature of about 30° C. or above, in other embodiments, the method is performed at a temperature of about 35° C. or above.

In a further aspect, the invention relates to a tip cap movement device for use in the method according to the invention.

In one embodiment, the invention relates to a device (11) for use in a method of the invention for determining the robustness of a seal of a flexible part of a container, wherein the flexible part comprises a sealing means, said sealing means is sealing the interior (1.1) of the container from the container exterior (1.2), the device comprising a) a holding unit (12) comprising means for holding the container in a fixed position, b) a moveable unit (13) having a means for moving (17) the flexible part (4) in a direction away from the container; and c) means for providing a fluid connection (9) between the interior of the container with a detection device for a test medium (10).

The container can be any container as defined herein, also with all its embodiments.

In a particular embodiment, the invention relates to a device (11) for use in a method of the invention for determining the sensitivity of a seal between a flexible part and a syringe, wherein the flexible part comprises a sealing means, said sealing means is sealing the interior (1.1) of the syringe from the syringe exterior (1.2), the device comprising a) a holding unit (12) comprising means for holding the syringe in a fixed position, and b) a moveable unit (13) having a means for moving (17) the flexible part (4) in a direction away from the syringe.

The flexible part is preferably a tip cap (4) and/or a plunger (2).

In one specific embodiment, the invention relates to a device (11) for use in a method of the invention for determining the sensitivity of a seal between a tip cap (4) and a syringe, said syringe comprising a barrel (1) and a tip (5), wherein the tip (5) is covered with the tip cap (4) such as to form said seal between the tip (5) and the tip cap (4), said device (11) comprising: a) a holding unit (12) comprising means for holding the syringe in a fixed position, and b) a moveable unit (13) having a means for moving (17) the tip cap (4) in a direction away from the syringe.

Figure 5A:
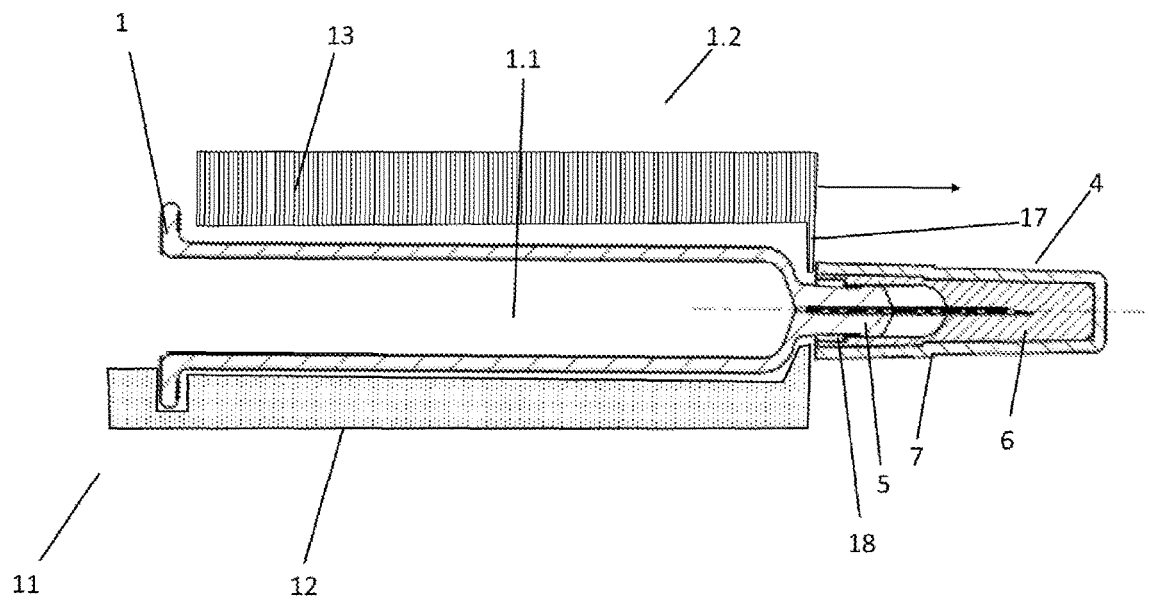
FIG. 5: Specific embodiment of the present invention. 5A: Schematic illustration of a first embodiment of a movement device according to the invention. 5B: Schematic illustration of an alternative embodiment of a device according to the invention.

A possible, non-limiting embodiment of the device is depicted in FIG. 5A.

In a further specific embodiment, the invention relates to a device (11) for use in a method of the invention for determining the sensitivity of a seal between a plunger (2) wherein the plunger comprises a sealing means, said device (11) comprising:

a) a holding unit (12) comprising means for holding the syringe in a fixed position, and b) a moveable unit (13) having a means for moving (17) the plunger (2) in a direction away from the syringe.

The device is in the following described and depicted with reference to the movement of a tip cap, but is not intended to be limited to tip cap movement. All descriptions are transferable to a device for the movement of a plunger.

Figure 5B:
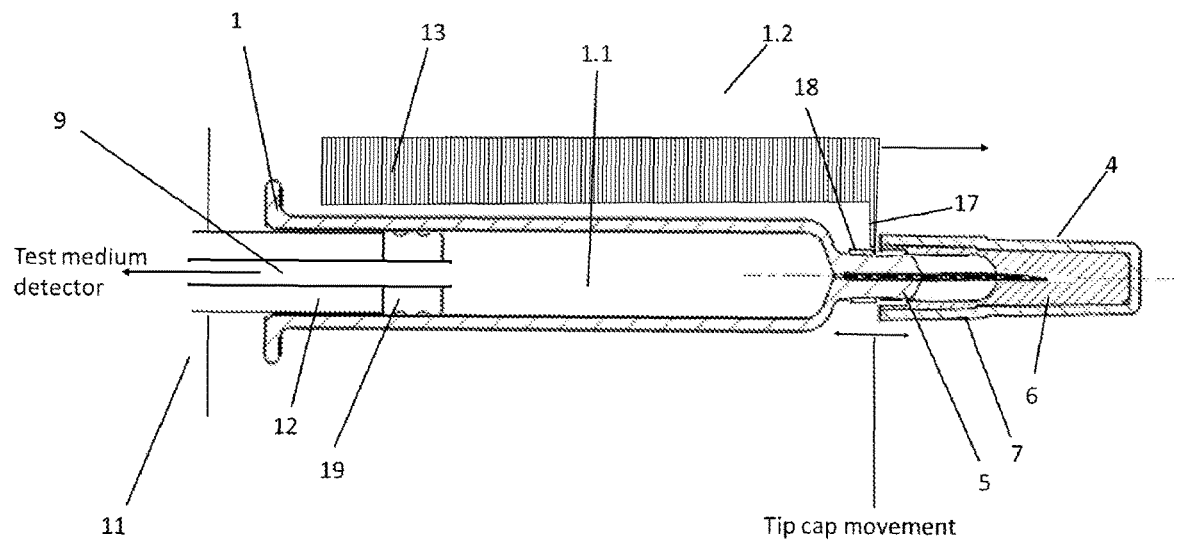
Figure 6A:
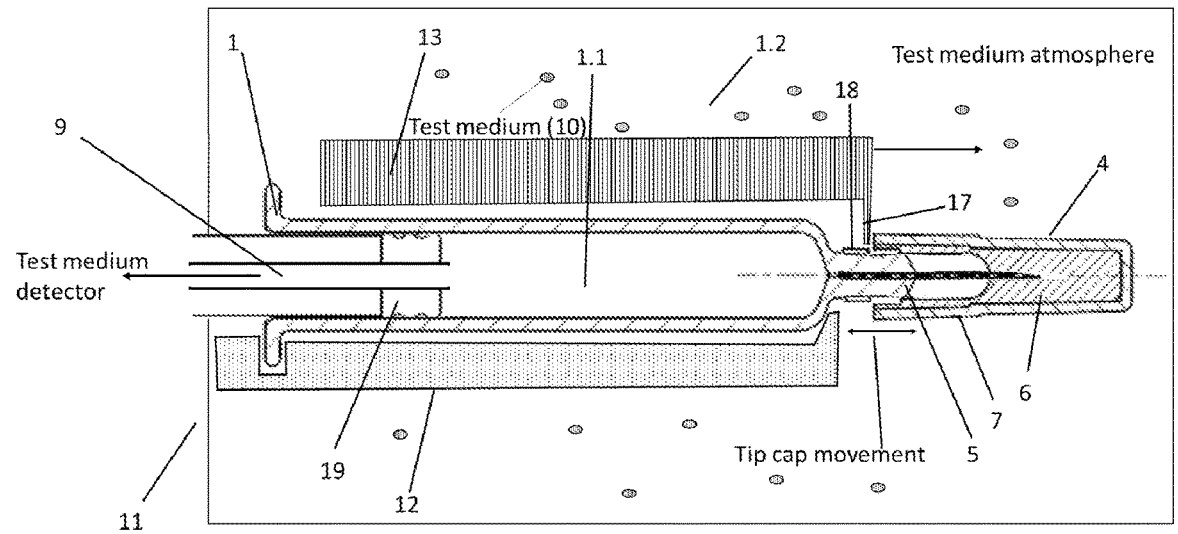
FIG. 6: Specific embodiment of the present invention. 6A: Illustration of a device according to the invention in use in the method of the invention. 6B: Illustration of an alternative device in use in the method of the invention.
Figure 6B:
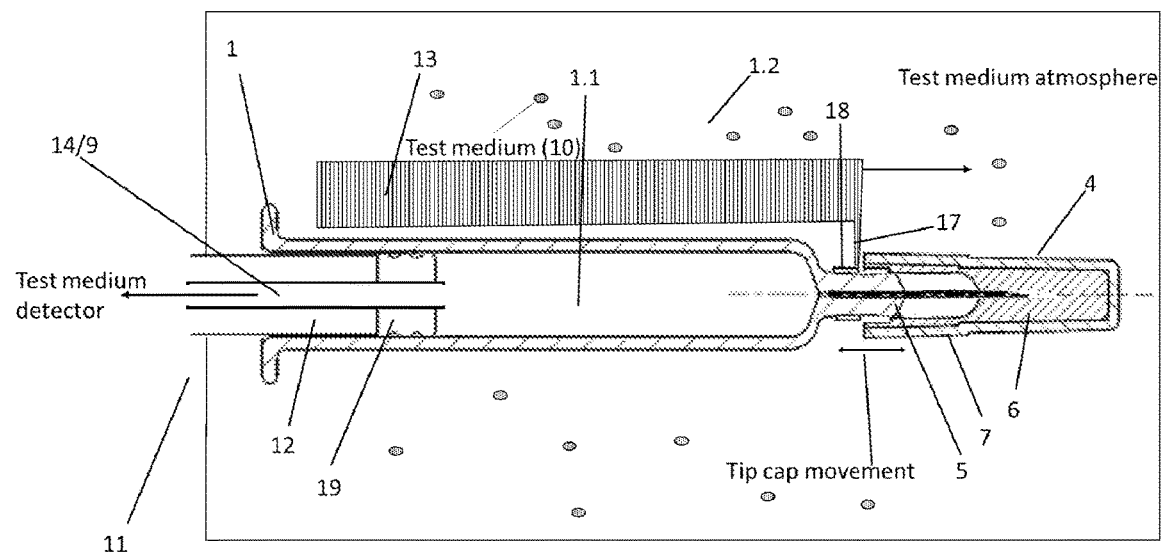

In some embodiments of the invention, the holding unit (12) additionally comprises a void (14) arranged to be in fluid connection with the interior space of the syringe (1.1), the void being connectable to a detector capable of detecting a test medium as means for providing a fluid connection (9) between the interior of the container with a detection device for a test medium (10). A non-limiting embodiment of this particular invention is depicted in FIG. 5B.

The device can be independent of the detection device used in the method. Preferably it is compatible and connectable to the detection device. In some embodiments, at least parts of the device are also part of the detection device (see e.g. FIG. 5B).

In some embodiments of the invention, the holding unit (12) and/or the moveable unit (13) are an integral part of a detection device. In a preferred embodiment of the invention, the holding unit (12) is part of the detection device. In an alternative embodiment, the holding unit (12) can be connected to a detection device. In some embodiments, the holding unit comprises a sealing means (19) to allow in combination with the tip cap and/or plunger sealing the interior of the syringe (1.1) from the exterior (1.2).

In a particular embodiment, the device comprises a sealing means (19), which allows the syringe interior to be evacuated, when connected to a detector.

In some embodiments, the holding unit (12) comprises means to connect to a detection device, without sealing means. In these embodiment, the detection device further requires means to ensure a fluid connection between the detection device and the syringe interior.

It is preferred that the moveable unit (13) allows movement in a defined direction, preferably along an axis defined by the syringe barrel, or alternatively defined by the direction in which the needle cannula extends. Preferably, the combination of moveable unit (12) and holding unit (13) allows a defined, preferably continuous and/or linear movement.

In a preferred embodiment of the invention, the holding unit (12) and the moveable unit (13) comprise compatible means to ensure a defined movement of the moving unit. Any means to ensure a defined movement is suitable and are known to the skilled person. In some embodiments, these means include surface modifications, such as small ribs or other surface structures. In some embodiments, these means comprise different materials at contact positions of the two units, such as for example silicone areas on each unit.

In a particular embodiment of the invention, said compatible means comprise compatible threads on both units. Compatible threats have the advantage of defined and compatible movement, ensuring also a movement in uniform direction.

In some embodiments, the moveable unit (13) of the device can be moved manually and/or automatically. In a particular embodiment, the moveable unit (13) can be moved manually. In a further embodiment, the moveable unit (13) can be moved manually. In some embodiments, the device allows both manual and automatic movement of the moveable unit (13).

The movement distance of the tip cap preferably corresponds or at least correlates to the movement of the moveable unit (13). The distance can be determined with any suitable method, such as for example a digital caliper, which can be operated manually or automatically. In a preferred embodiment, the holding unit (12) provides at least one reference point, which allows the determination of the movement distance.

In a further specific embodiment, the device (11) comprises means to determine the movement distance of the movement unit.

The device (11) might be made of any suitable material or material combinations. In some embodiments, the moveable unit (13) and the holding unit (12) are at least partly made of the same material. In a different embodiment, the moveable unit (13) and the holding unit (29 are made of different materials or material combinations.

In some embodiments, the moveable unit (13) and/or the holding unit (12) are at least partly made of metal, a metal alloy or a polymer. In a specific embodiment of the invention, the moveable unit (13) and/or the holding unit (12) are at least partly made of metal. In a preferred embodiment of the invention, said metal is steel or aluminium.

In a further aspect, the invention relates to the use of the device as defined above in a method as defined above.

Examples

Material & Methods

Syringes and Components 5 glass syringes and 1 polymeric syringe featuring a staked-in needle cannula and a tip cap were used (Table 1).

TABLE 1

Syringe configurations used

| Sample | Manufacturer of syringe | Volume of syringe | Material of barrel of syringe | Manufacturer of tip cap |
|---|---|---|---|---|
| S1 | A | 1 mL | Glass | D |
| S2 | A | 2.25 mL | Glass | D |
| S3 | B | 1 mL | Glass | B |
| S4 | C | 1 mL | Glass | D |
| S5 | C | 2.25 mL | Glass | D |
| S6 | A | 1 mL | COP | D |

Helium Leak CCIT

To analyse the container closure integrity of syringes in a method according to the invention, an air tight flange was mounted on an ASM340 mass spectrometric helium leak detector (Pfeifer Vacuum, Asslar, Germany). Helium Leak CCIT was measured by fixing the the barrel, that is the plunger side, of the syringe on the helium leak flange. A chamber (21) was attached to the flange and helium gas was applied, resulting in a saturated helium atmosphere (>95% He) in the chamber (see FIG. 3A).

According to the US Pharmacopeia, a PFS was considered as tight below the cut-off value of $6*10^{-6}$ mbarL/s (USP<1207>, Package Integrity Evaluation-Sterile Products. pp 1700-1707). Accordingly, this flow rate was used as threshold.

CCIT of a Glass and a Polymeric Syringe at Different Time Points of Measurement

A time series of helium leak measurement was performed over 12 min to investigate a possible impact of gas permeability of polymer syringes on measured helium leak rates without movement of the flexible part.

Figure 8:
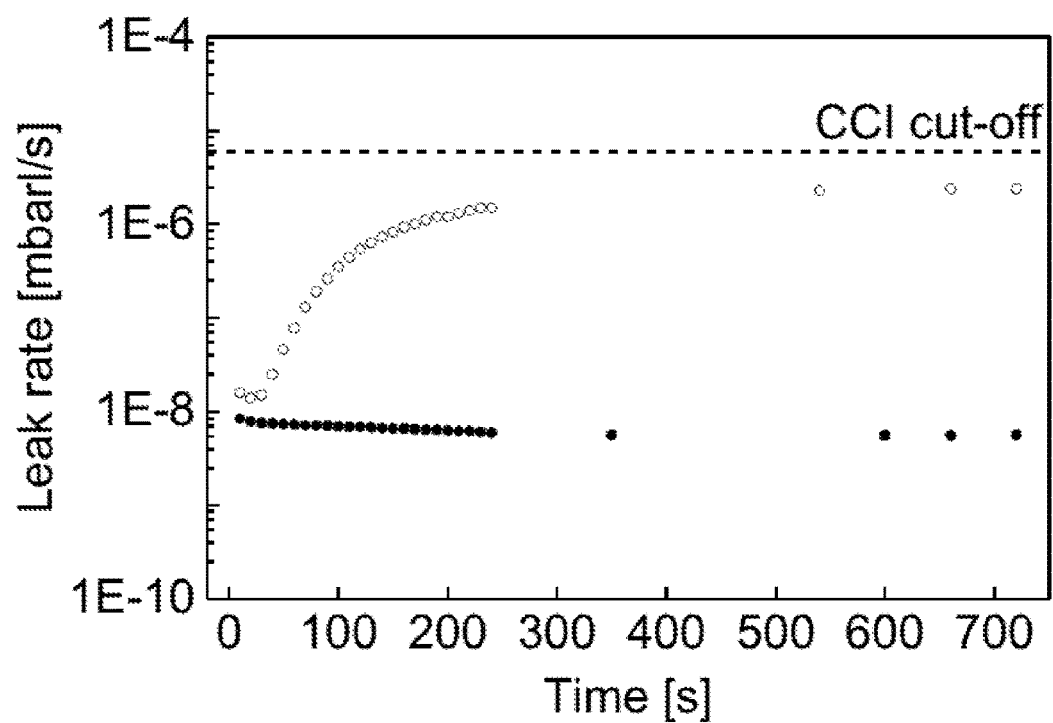
FIG. 8. Inherent Helium leak rates of a glass syringe S2 (solid circles) and an intact polymeric syringe S6 (open circles) over time (12 minutes) without tip cap movement.

A glass syringe shows a negligible decrease in the detected He-flow rate over the observed time period from $8.5 \times 10^{-9}$ mbar*L/s after 10 seconds to $5.7 \times 10^{-9}$ mbar*L/s after 12 minutes, which is associated to vacuum build up (see FIG. 8).

In contrast, a polymeric syringe showed an inherent increase in helium leak rates starting after about 30 seconds (see FIG. 8). The increase of helium leak rates can for example be explained by diffusion of helium gas through the polymer barrel of the PFS. However, the leak rates of the polymeric syringe stayed well below the CCI threshold defined above.

Assessment of Tip Cap Sensitivity

Figure 7:
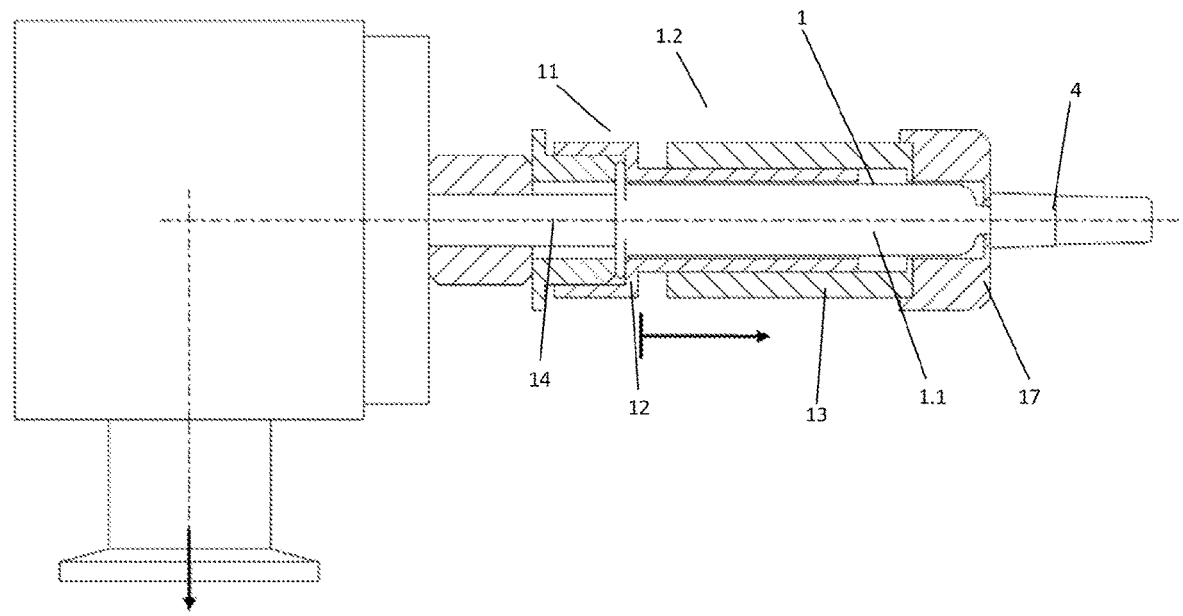
FIG. 7: Exemplary tip cap movement device attached to a PFS mounted to the helium leak adapter for CCIT of PFS.

Assessment of acceptable tip cap movement without compromising CCI was determined by using a tip-cap movement device according to the invention (FIGS. 5 and 7). The barrel of the syringe was fixed at the flange into the tip cap movement device and mounted on the syringe adapter. The maximum acceptable tip cap movement was then obtained by slowly separating the tip cap from the syringe cone while constantly applying helium gas. The tip cap movement rate was 0.2 mm per 10 seconds. The maximum acceptable tip cap movement was then determined at the tip cap movement device by measuring the distance with a digital caliper between the initial tip cap position and the position at which CCI was compromised, that is at which the threshold value was reached.

Figure 9:
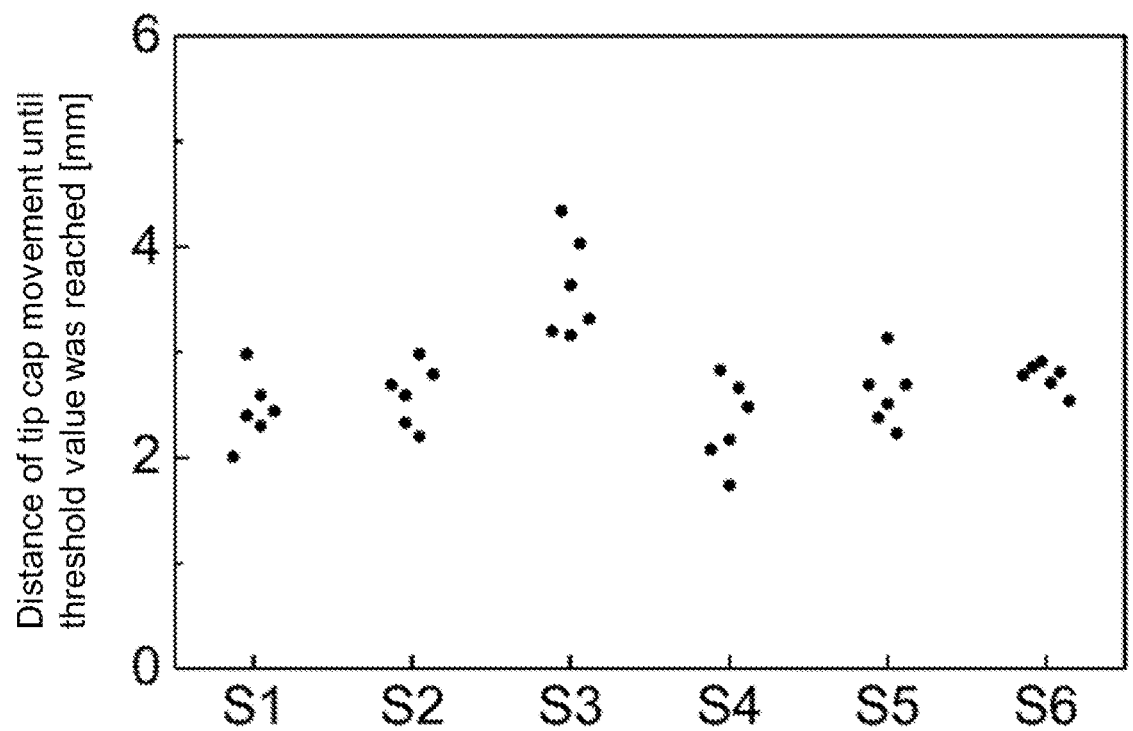
FIG. 9. Determination of tip cap movement of 6 PFS (n=6) without compromising CCI.

The results are shown in FIG. 9. Tip caps of all tested syringes could be moved for at least 1.7 mm. All tested syringes featuring different syringe barrel/RNS combination showed tip cap movement between 1.74 mm and 4.34 mm, until the threshold value was reached, and showed only small variations.

The figure also shows that the method produces reproducible results for identical tip cap and syringe combinations. As such the method is suitable for quality control.

The invention claimed is:

1. A method for determining the robustness of a seal of a flexible part of a container comprising the steps of:
    a) providing a container comprising at least one flexible part, wherein said at least one flexible part comprises a sealing means;
    b) said sealing means is sealing the interior of the container from the exterior of the container;
    c) providing a fluid connection between the interior of the container with a detection device for a test medium;
    d) exposing the exterior of the container to an atmosphere comprising said test medium;
    e) moving the flexible part of the container in a direction away from the container until the detection device detects the test medium above a predefined threshold value;
    f) determining the distance by which the flexible part was moved in step e).

2. The method according to claim 1, wherein the flexible part is a cap, a stopper or a plunger.

3. The method according to claim 1, wherein the container is a syringe or a cartridge or a vial.

4. The method according to claim 1, wherein the container is a syringe and the method comprises the steps of:
    a) providing a syringe comprising a barrel and at least one flexible part, wherein said at least one flexible part comprises a sealing means;
    b) said sealing means is sealing the interior of the syringe from the exterior of the syringe;
    c) providing a fluid connection between the interior of the syringe with a detection device for a test medium;
    d) exposing the exterior of the syringe to an atmosphere comprising said test medium;
    e) moving the flexible part of the syringe in a direction away from the syringe until the detection device detects the test medium above a predefined threshold value;
    f) determining the distance by which the flexible part was moved in step e).

5. The method according to claim 4, wherein the at least one flexible part is a tip cap and the method comprises the steps of:
    a) providing a syringe comprising a barrel and a tip, wherein the tip is covered with the tip cap such as to form a seal between the tip and the tip cap;
    b) said seal is sealing the interior of the syringe against the exterior of the syringe;
    c) providing a fluid connection between the interior of the syringe with a detection device for a test medium;
    d) exposing the exterior of the syringe to an atmosphere comprising said test medium;
    e) moving the tip cap of the syringe in a direction away from the syringe until the detection device detects the test medium above a predefined threshold value;
    f) determining the distance by which the tip cap was moved in step e).

6. The method according to claim 4, wherein the flexible part is a plunger and the method comprises the steps of:
    a) providing a syringe comprising a barrel and a plunger, wherein the plunger comprises a sealing means;
    b) said sealing means is sealing the interior of the syringe against the exterior atmosphere;
    c) providing a fluid connection between the interior of the syringe with a detection device for a test medium;

d) exposing the exterior of the syringe to an atmosphere comprising said test medium;
e) moving the plunger of the syringe in a direction away from the syringe until the detection device detects the test medium above a predefined threshold value;
f) determining the distance by which the plunger was moved in step e).

7. The method according to claim 1, wherein the test medium is a gas.

8. The method according to claim 1, wherein the test medium is He and the detector is a mass spectrometric He detector.

9. The method according to claim 1, wherein the exterior of the container is exposed an atmosphere comprising the test medium.

10. The method according to claim 9, wherein the container is exposed an atmosphere comprising at least 95% (v/v) of test medium.

11. The method according to claim 1, wherein the flexible part is moved with a moving apparatus.

12. The method according to claim 1, wherein the method is performed at room temperature.

13. A device for use in a method for determining the robustness of a seal of a flexible part of a container, wherein the flexible part comprises a sealing means, said sealing means is sealing the interior of the container from the container exterior, the device comprising
   a) a holding unit comprising means for holding the container in a fixed position,
   b) a moveable unit having a means for moving the flexible part in a direction away from the container;
   c) means for providing a fluid connection between the interior of the container with a detection device for a test medium; and
   d) means for determining the distance the flexible part is moved.

14. The device according to claim 13, wherein the container is a syringe.

15. The device according to claim 13, wherein the container is a syringe comprising a barrel and a tip and the flexible part is a tip cap, wherein the tip of the syringe is covered with the tip cap.

16. The device according to claim 13, wherein the container is a syringe and the flexible part is a plunger.

17. The device according to claim 13, wherein the holding unit additionally comprises a void arranged to be in fluid connection with the interior space of the container, the void being connectable to a detector capable of detecting a test medium as means for providing a fluid connection between the interior of the container with a detection device for a test medium.

18. The device according to claim 13, wherein the holding unit or the moveable unit, or both the holding unit and the movable unit are an integral part of a detection device.

19. The device according to claim 13, wherein the holding unit and the moveable unit comprise compatible means to ensure a defined movement of the moving unit.

20. The device according to claim 19, wherein said compatible means comprise compatible threads on both units.

21. The device according to claim 13, wherein the moveable unit of the device can be moved manually and/or automatically, or both manually and automatically.

* * * * *